US 6,669,925 B1

(12) United States Patent
Mach et al.

(10) Patent No.: US 6,669,925 B1
(45) Date of Patent: Dec. 30, 2003

(54) SIGMA-2 RECEPTORS AS BIOMARKERS OF TUMOR CELL PROLIFERATION

(75) Inventors: Robert H. Mach, Winston-Salem, NC (US); Kenneth T. Wheeler, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/844,263

(22) Filed: Apr. 27, 2001

Related U.S. Application Data

(60) Provisional application No. 60/200,052, filed on Apr. 27, 2000.

(51) Int. Cl.$^7$ .................. A61K 51/00; A61M 36/14
(52) U.S. Cl. ................ 424/9.1; 424/1.11; 424/1.65; 424/9.2; 534/14; 540/450
(58) Field of Search ................ 424/1.11, 1.65, 424/1.85, 1.89, 9.1, 9.2; 540/450; 534/7, 10–16

(56) References Cited

U.S. PATENT DOCUMENTS

| | | | | |
|---|---|---|---|---|
| 4,797,387 | A | 1/1989 | King | 514/212 |
| 4,808,588 | A | 2/1989 | King | 514/212 |
| 5,106,843 | A | 4/1992 | Ward et al. | 514/213 |
| 5,223,511 | A | * 6/1993 | Turconi et al. | 514/304 |
| 5,330,990 | A | 7/1994 | Hansen | 514/299 |
| 6,113,877 | A | * 9/2000 | Mach et al. | 424/1.65 |

FOREIGN PATENT DOCUMENTS

| | | | |
|---|---|---|---|
| EP | 0747355 | 12/1996 | ......... C07D/211/46 |
| WO | 93/08185 | 4/1993 | ......... C07D/451/04 |
| WO | 95/21820 | 8/1995 | ......... C07D/211/46 |
| WO | 97/34892 | 9/1997 | ......... C07D/451/02 |

OTHER PUBLICATIONS

Bermudez, J., et al., "5–Hydroxytryptamine (5–HT3) Receptor Antagonists. 3. Ortho–substituted Phenylureas", *J. Med. Chem., 33*, pp. 193–1935, (1990).

Kline, R.H., et al., "Synthesis of 3–carbamoylecgonine Methyl Ester Analogues as Inhibitors of Cocaine Binding and Dopamine Uptake", *J. Med. Chem.*, 34, pp. 702–705, (1991).

Turconi, M., et al., "Synthesis of a New Class of 2, 3–Dihydro–2–oxo–1H–benzimidazole–1carboxylic Acid Derivatives as Highly Potent 5–HT3 Receptor Antagonists", *J. Med. Chem., 33*, pp. 2101–2108, (1990).

Vilner, B.J., et al., "Sigma–1 and Sigma–2 Receptors Are Expressed in a Wide Variety of Human and Rodent Tumor Cell Lines", *Cancer Research, 55* (2), pp. 408–413, (1995).

\* cited by examiner

*Primary Examiner*—Dameron L. Jones
(74) *Attorney, Agent, or Firm*—Myers Bigel Sibley & Sajovec, PA

(57) ABSTRACT

The present invention provides novel sigma-2 ligands (labeled and unlabeled) and the use of the compounds in medical therapy or diagnosis.

21 Claims, 4 Drawing Sheets

6a

6b

6c

6d

6e

6f

Re-MAMA-6b

7a

7b

7c

7d

7e

SIGMA-2 RECEPTORS AS BIOMARKERS OF TUMOR CELL PROLIFERATION

CROSS-REFERENCE TO RELATED APPLICATION

This application claims priority to U.S. Provisional Application Ser. No. 60/200,052 filed Apr. 27, 2000; which is incorporated herein by reference.

BACKGROUND OF THE INVENTION

Breast cancer is characterized by a proliferative potential that can vary considerably from patient to patient. The rate of cell proliferation has been shown in breast tumors to predict the response to radiation therapy and chemotherapy. Presently, measures of cell proliferation are obtained by histological or flow-cytometric analysis. Both methods are limited by sampling procedures and only 60–70% of patient samples are suitable for flow cytometric analysis.

It was recently demonstrated that sigma-2 ($\sigma$2) receptors are expressed in high density in a number of human and rodent breast cancer cell lines (*Cancer Research*, 55, 408 (1995)). However, their expression is heterogenous, and their function is unknown.

Compounds suitable for noninvasive methods that can accurately assess the proliferative status of breast cancer are disclosed, e.g., in U.S. application Ser. No. 60/013717, filed Mar. 30, 1996; in U.S. application Ser. No. 09/142935, filed Sep. 17, 1998; and in U.S. application Ser. No. 09/528398, filed Mar. 20, 2000. However, additional sigma-2 receptor ligands (e.g., therapeutic agents or imaging agents) are needed. Preferred ligands will demonstrate high selectivity for $\sigma_2$ versus $\sigma_1$ receptors or show increased binding for sigma receptors.

A continuing need exists for noninvasive methods that can accurately assess the proliferative status of breast cancer and for novel therapeutic agents useful for treating cancer.

SUMMARY OF THE INVENTION

It has surprising been discovered that compounds of the invention demonstrate high selectivity for $\sigma_2$ versus $\sigma_1$ receptors or show increased binding for sigma receptors, over sigma receptors. In addition, it has surprisingly been discovered that compounds of the present invention having two to ten, and preferably 2 to 3 carbon atoms separating the aryl group and the nitrogen atom of the bicyclic ring, demonstrate high selectivity for $\sigma_2$ versus $\sigma_1$ receptors or show increased binding for sigma receptors, over the corresponding compounds having only one carbon atom separating the aryl group and the nitrogen atom of the bicyclic ring.

The present invention provides a compound of formula (I):

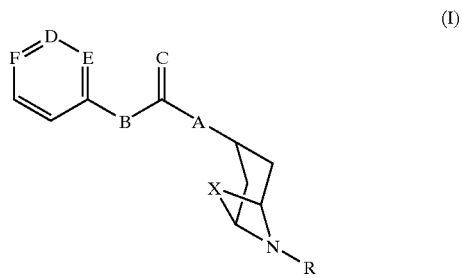

wherein
R is aryl-Y—;
Y is a divalent ($C_2$–$C_{10}$)alkyl, ($C_2$–$C_{10}$)alkenyl, or ($C_2$–$C_{10}$)alkynyl chain optionally comprising one or more —O—, —S—, or N(Z) in the chain and is optionally substituted on carbon with one or more oxo (=O);
aryl is optionally substituted with one or more halo, OH, ($C_1$–$C_6$)alkyl, ($C_1$–$C_6$)alkoxy, ($C_1$–$C_6$)C(O), ($C_1$–$C_6$)alkyl-S, $NH_2$, SH, N(Z)$_2$;
A is NH, O or S;
B is NH, O or S;
C is O or S;
D is CH or N;
E is CH or N;
F is CH or N; and
X is ($CH_2$)$_2$, ($CH_2$)$_3$ or CH=CH;
each Z is H or ($C_1$–$C_6$)alkyl;
wherein the ring comprising F=D—E is optionally substituted with one or more halo, OH, ($C_1$–$C_6$)alkyl, ($C_1$–$C_6$)alkoxy, ($C_1$–$C_6$)C(O), ($C_1$–$C_6$)alkyl-S, $NH_2$, SH, N(Z)$_2$, wherein Z is H or ($C_1$–$C_6$)alkyl, or methylene dioxy (—OCH$_2$O—);
or a pharmaceutically acceptable salt thereof The present invention also provides a compound of formula (I):

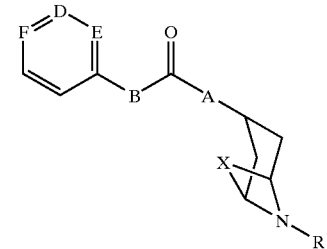

wherein
R is aryl-Y—;
Y is a divalent ($C_2$–$C_{10}$)alkyl, ($C_2$–$C_{10}$)alkenyl, or ($C_2$–$C_{10}$)alkynyl chain optionally comprising one or more —O—, —S—, or N(Z) in the chain and is optionally substituted on carbon with one or more oxo (=O);
aryl is optionally substituted with one or more halo, haloalkyl, OH, ($C_1$–$C_6$)alkyl, ($C_1$–$C_6$)alkoxy, ($C_1$–$C_6$)C(O), ($C_1$–$C_6$)alkyl-S, $NH_2$, SH, N(Z)$_2$;
A is NH, O or S;
B is NH, O, or S;

C is O or S;

D is CH or N;

E is CH or N;

F is CH or N; and

X is (CH$_2$)$_2$, (CH$_2$)$_3$ or CH=CH;

each Z is H or (C$_1$–C$_6$)alkyl;

wherein the ring comprising F=D—E is optionally substituted with one or more halo, OH, (C$_1$–C$_6$)alkyl, haloalkyl, (C$_1$–C$_6$)alkoxy, (C$_1$–C$_6$)C(O), (C$_1$–C$_6$)alkyl-S, NH$_2$, SH, N(Z)$_2$, wherein Z is H or (C$_1$–C$_6$)alkyl, or methylene dioxy (—OCH$_2$O—);

or a pharmaceutically acceptable salt thereof.

The present invention also provides a compound of formula (II):

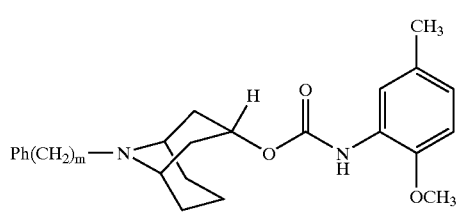

wherein m is 2–7.

The present invention also provides a compound of formula (I):

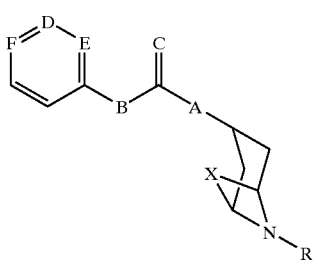

wherein

R is a —L-Det;

L is a divalent (C$_2$–C$_{10}$)alkyl, (C$_2$–C$_{10}$)alkenyl, or (C$_2$–C$_{10}$)alkynyl chain optionally comprising one or more —O—, —S—, or N(Z) in the chain and is optionally substituted on carbon with one or more oxo (=O);

A is NH, O or S;

B is NH, O, or S;

C is O or S;

D is CH or N;

E is CH or N;

F is CH or N;

X is (CH$_2$)$_2$, (CH$_2$)$_3$ or CH=CH;

wherein the ring comprising F=D—E is optionally substituted with one or more halo, OH, (C$_1$–C$_6$)alkyl, (C$_1$–C$_6$)alkoxy, (C$_1$–C$_6$)C(O), (C$_1$–C$_6$)alkyl-S, NH$_2$, SH, N(Z)$_2$, wherein Z is H or (C$_1$–C$_6$)alkyl, or methylene dioxy (—OCH$_2$O—);

Z is H or (C$_1$–C$_6$)alkyl;

Det is

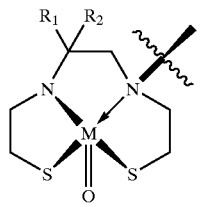

wherein

M is Technetium-99m or Rhenium-186;

R$_1$ and R$_2$ are each independently H or together are oxo;

or a pharmaceutically acceptable salt thereof.

The present invention also provides a compound of formula (I):

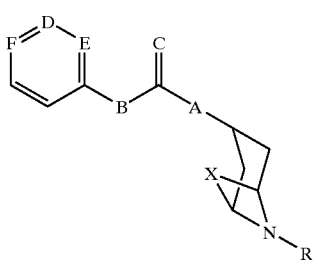

wherein

R is a —L-Det;

L is a divalent (C$_2$–C$_{10}$)alkyl, (C$_2$–C$_{10}$)alkenyl, or (C$_2$–C$_{10}$)alkynyl chain optionally comprising one or more —O—, —S—, or N(Z) in the chain and is optionally substituted on carbon with one or more oxo (=O);

A is NH, O or S;

B is NH, O, or S;

C is O or S;

D is CH or N;

E is CH or N;

F is CH or N;

X is (CH$_2$)$_2$, (CH$_2$)$_3$ or CH=CH;

wherein the ring comprising F=D—E is optionally substituted with one or more halo, OH, (C$_1$–C$_6$)alkyl, (C$_1$–C$_6$)alkoxy, (C$_1$–C$_6$)C(O), (C$_1$–C$_6$)alkyl-S, NH$_2$, SH, N(Z)$_2$, wherein Z is H or (C$_1$–C$_6$)alkyl, or methylene dioxy (—OCH$_2$O—);

Z is H or (C$_1$–C$_6$)alkyl;

Det is

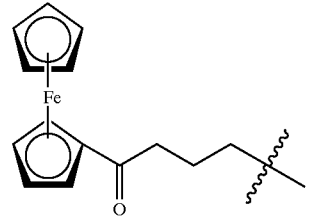

The present invention also provides a compound of formula (III):

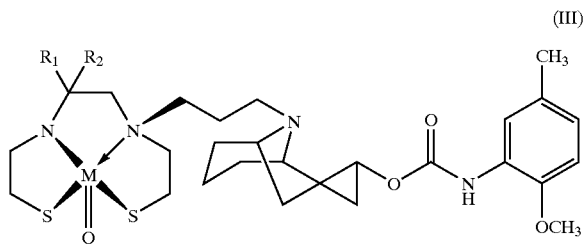

(III)

wherein

M is Technetium-99m or Rhenium-186; and $R_1$ and $R_2$ are each independently H or together are oxo.

The present invention also provides a pharmaceutical composition comprising a compound of the invention and a pharmaceutically acceptable carrier.

The present invention also provides a method to determine the proliferative status of a cancer cell comprising:

(a) administering to a human afflicted with a solid tumor, an amount of a detectably-labeled compound of the present invention; and (b) determining the extent to which the compound binds to cells of the tumor, the extent providing a measure of the proliferative status of the cells.

The present invention also provides a compound of the present invention for use in medical therapy or diagnosis.

The present invention also provides a radiolabeled compound of the present invention (e.g., a compound of formula (I) or (II)).

The present invention also provides the use of a compound of the present invention for the manufacture of a medicament for imaging a tumor in a mammal.

The present invention also provides an unlabeled compound of the present invention (e.g., a compound of formula (I)) useful as a therapeutic agent for treating diseases wherein sigma-2 activity is implicated and modulation (e.g., antagonism or agonism) of sigma-2 activity is designed.

DETAILED DESCRIPTION OF THE INVENTION

Figure 1:
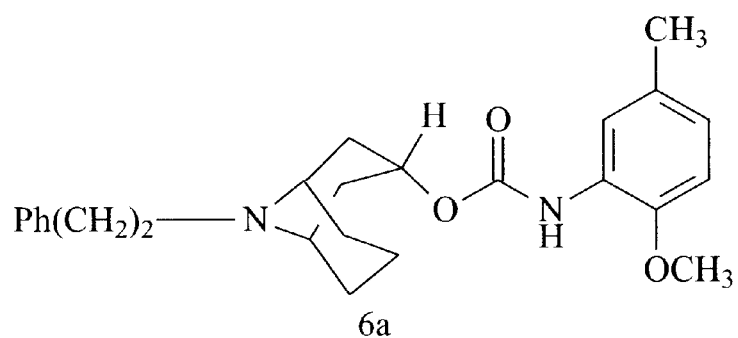
FIG. 1 shows compounds of the invention.
Figure 1:
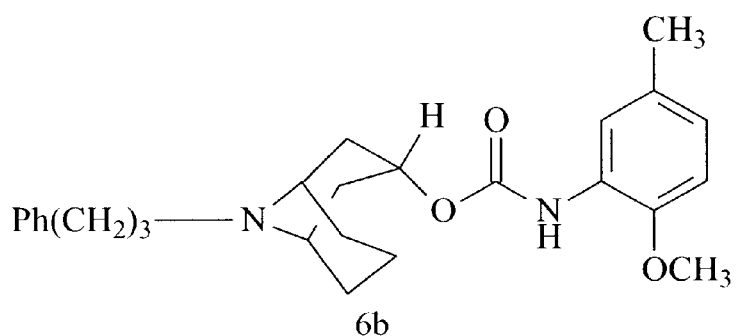
Figure 1:
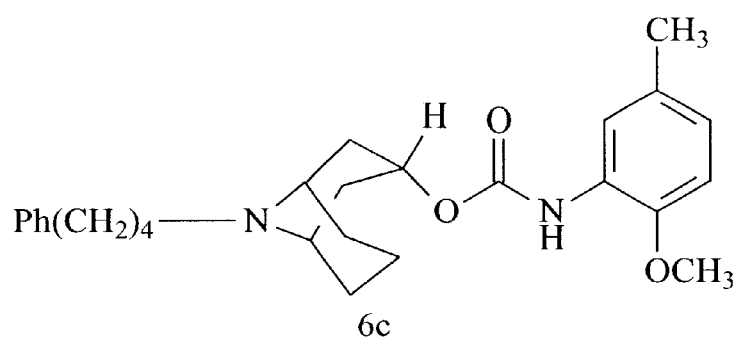
Figure 2:
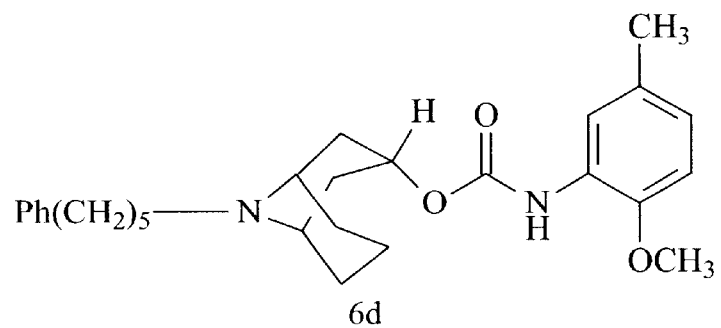
FIG. 2 shows compounds of the invention.
Figure 2:
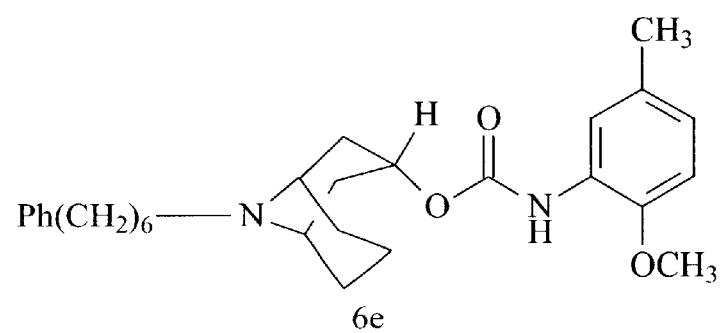
Figure 2:
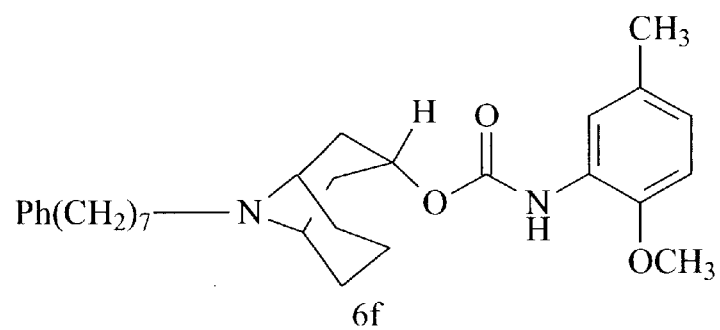
Figure 2:
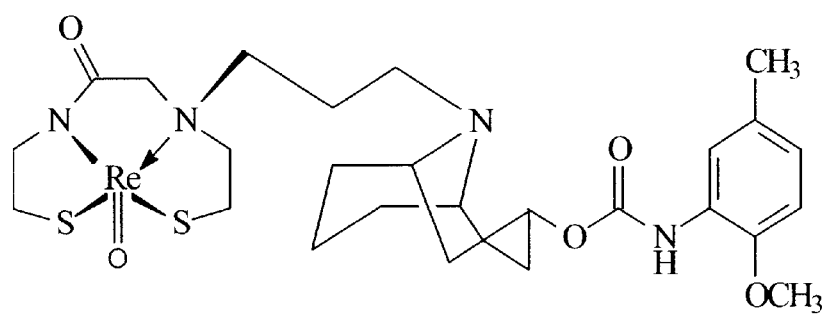
Figure 3:
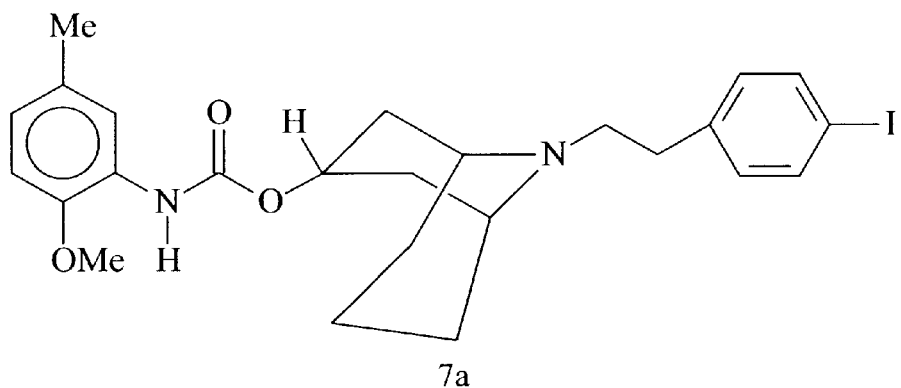
FIG. 3 shows compounds of the invention.
Figure 3:
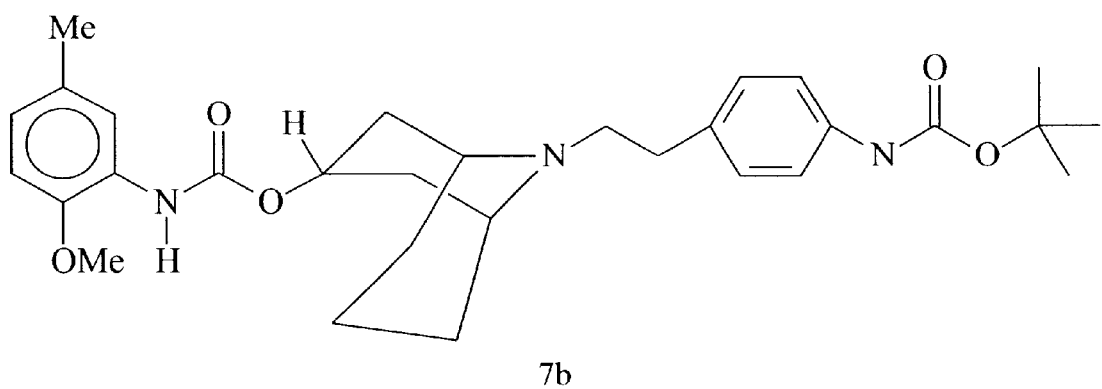
Figure 3:
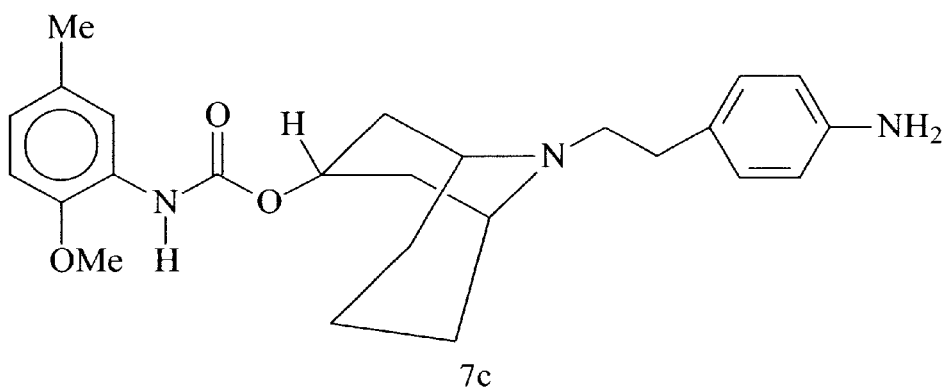
Figure 4:
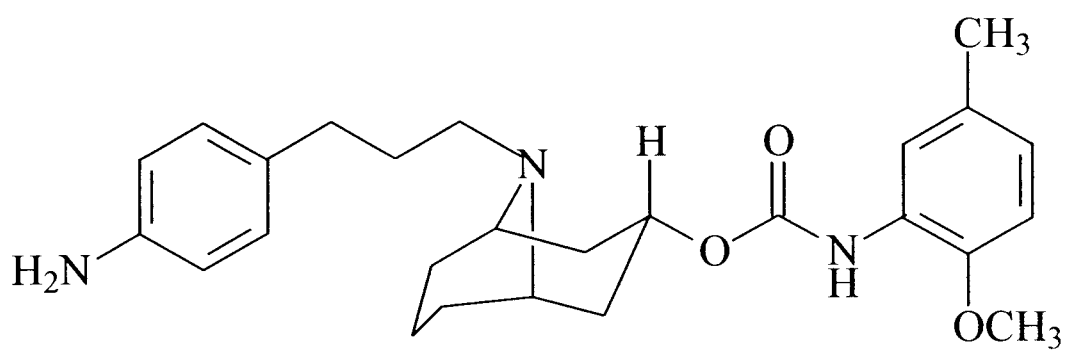
FIG. 4 shows compounds of the invention.
Figure 4:
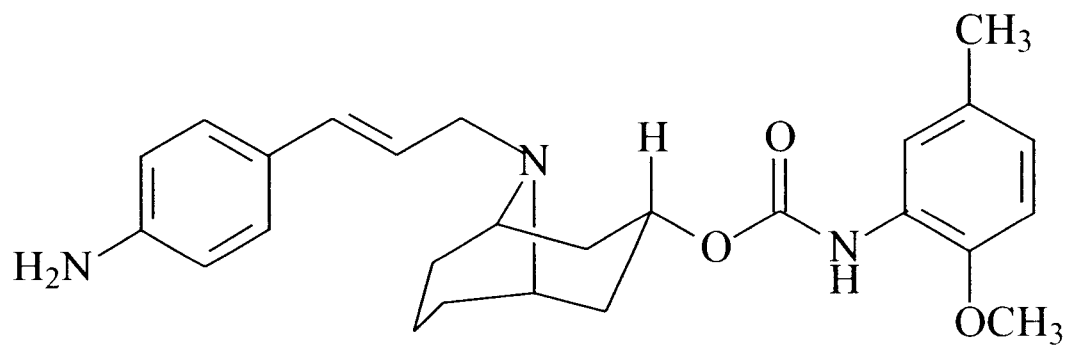

The following definitions are used, unless otherwise described: halo is fluoro, chloro, bromo, or iodo. Alkyl, alkoxy, alkenyl, etc. denote both straight and branched groups. Aryl denotes a phenyl radical or an ortho-fused bicyclic carbocyclic radical having about nine to ten ring atoms in which at least one ring is aromatic.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine σ-2 activity using the standard tests described herein, or using other similar tests which are well known in the art.

Specific values listed below for radicals, substituents and ranges, are for illustration only; they do not exclude other defined values or other values within defined ranges for the radicals and substituents.

Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl, or decyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_{10})$ alkenyl can be vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl; $(C_2-C_{10})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1- hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl; aryl can be phenyl, indenyl, or naphthyl.

The term "halo" or "halogen" refers to fluoro, chloro, bromo and iodo.

"Haloalkyl" refers to alkyl as defined herein substituted by 1–4 halo groups as defined herein, which may be the same or different. Representative haloalkyl groups include, by way of example, trifluoromethyl, trifluoroethyl, 3-fluorododecyl, fluoroethyl, 12,12,12-trifluorododecyl, 2-bromooctyl, 3-bromo-6-chloroheptyl, and the like.

The term "alkenyl" refers to a monoradical of a branched or unbranched unsaturated hydrocarbon group preferably having from 2 to 10 carbon atoms, more preferably 2 to 8 carbon atoms and even more preferably 2 to 6 carbon atoms and having at least 1 and preferably from 1–4 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "alkoxy" refers to the groups alkyl-O—, alkenyl-O—, or cycloalkyl-O—, where alkyl, alkenyl or cycloalkyl, are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

Specifically, the compounds of the present invention (e.g., the compound of formula (I) or (II)) can be detectable labeled.

Specifically, the label comprises a radionuclide.

Specifically, E, D and F can be CH.

Specifically, B is NH and A can be O.

Specifically, the ring comprising F=D—E can be substituted with $(C_1-C_6)$alkyl, $(C_1-C_6)$alkoxy, or any combination thereof.

Specifically, the ring comprising F=D—E can be substituted with $(C_1-C_6)$alkyl, $(C_1-C_6)$alkoxy, haloalkyl, or any combination thereof.

Specifically, the ring comprising F=D—E can be substituted with $(C_1-C_6)$alkyl, $(C_1-C_6)$alkoxy, fluoroalkyl, or any combination thereof.

Specifically, the ring comprising F=D—E can be substituted with $(C_1-C_6)$alkyl, $(C_1-C_6)$alkoxy, trifluoroalkyl, or any combination thereof.

Specifically, the ring comprising F=D—E can be substituted with $(C_1-C_6)$alkoxy, haloalkyl, or any combination thereof.

Specifically, the ring comprising F=D—E can be substituted with methyl, methoxy, or any combination thereof.

Specifically, the ring comprising F=D—E can be substituted with methyl, methoxy, fluoroethyl, or any combination thereof.

Specifically, the ring comprising F=D—E can be substituted with methyl, methoxy, trifluoroethyl, or any combination thereof.

Specifically, the ring comprising F=D—E can be substituted with, methoxy, fluoroethyl, or any combination thereof.

Specifically, the ring comprising F=D—E can be substituted with, methoxy, trifluoroethyl, or any combination thereof.

Specifically, aryl can be phenyl.

Specifically, aryl can be phenyl optionally substituted with one or more $NH_2$.

Specifically, aryl can be phenyl optionally substituted with one or more haloalkyl.

Specifically, aryl can be phenyl optionally substituted with one or more fluoroalkyl.

Specifically, aryl can be phenyl optionally substituted with one or more fluoroethyl.

Specifically, aryl can be phenyl optionally substituted with one or more trifluoroethyl.

Specifically, Y can be $(C_2-C_{10})$alkyl.

Specifically, Y can be n-ethylene, n-propylene, n-butylene, n-pentylene, n-hexylene, or n-heptylene.

Specifically, Y can be $(C_2-C_{10})$alkenyl.

Specifically, Y can be n-ethenylene, n-propenylene, n-butenylene, n-pentenylene, n-hexenylene, or n-hepentylene.

Specifically, Y can be n-prop-2,3-enylene (e.g., —CH=CH—$CH_2$—).

Specifically, X can be $(CH_2)_3$.

Processes and novel intermediates useful for preparing compounds of the present invention are provided as further embodiments of the invention. Additional intermediates useful for preparing compounds of the present invention and/or processes useful for making the same are disclosed in Meltzer et al., J. Med. Chem., 1997, 40, p.1835; Schibli, J. Labelled Cpd. Radiopharm., 1999, 42, suppl. 1, s147–149; Cesati, R., J. Labelled Cpd. Radiopharm., 1999, 42, suppl. 1, s150–152; U.S. Provisional Patent Application Serial No. 60/200,052 filed Apr. 27, 2000; and references cited therein.

A Compound of formula (I) or (II), wherein R is Ph$(CH_2)_m$ and m is 2–7, can be prepared by reacting the corresponding compound of formula (I) or (II), wherein R is H, with a suitable haloalkylphenyl compound (e.g., Ph$(CH_2)_m$ Cl, wherein m is 2–7). Suitable reaction conditions are known to those of skill in the art. See, e.g., March, *Advanced Organic Chemistry, Reactions, Mechanisms and Structure*, $2^{nd}$ Ed., 1977 and Carey & Sundberg, *Advanced Organic Chemistry, Part B: Reactions*, $2^{nd}$ Ed., 1983.

A compounds of formula (I) or (II), wherein R is H, can be prepared by catalytically hydrogenating (i.e., reducing) the corresponding compound of formula (I) or (II), wherein R is benzyl, employing hydrogen gas and a catalyst (e.g., Pearlman's Catalyst). Suitable reaction conditions are known to those of skill in the art. See, e.g., March, *Advanced Organic Chemistry, Reactions, Mechanisms and Structure*, $2^{nd}$ Ed., 1977 and Carey & Sundberg, *Advanced Organic Chemistry, Part B: Reactions*, $2^{nd}$ Ed., 1983.

Compounds of the present invention wherein A is oxygen and B is nitrogen can generally be prepared by reacting a corresponding isocyanate with an alcohol under standard conditions. Solvents, bases, and reaction conditions suitable for such a reaction are well known to the art. See, e.g., March, *Advanced Organic Chemistry, Reactions, Mechanisms and Structure*, $2^{nd}$ Ed., 1977 and Carey & Sundberg, *Advanced Organic Chemistry. Part B: Reactions*, $2^{nd}$ Ed., 1983.

Compounds of the present invention wherein A is nitrogen and B is nitrogen can generally be prepared by reacting a corresponding isocyanate with an amine under standard conditions. Solvents, bases, and reaction conditions suitable for such a reaction are well known to the art. , e.g., March, *Advanced Organic Chemistry, Reactions, Mechanisms and Structure*, $2^{nd}$ Ed., 1977 and Carey & Sundberg, *Advanced Organic Chemistry, Part B: Reactions*, $2^{nd}$ Ed., 1983.

It is noted that many of the starting materials employed in the synthetic methods described above are commercially available, are reported in the scientific literature, or can be prepared using methods analogous to those described in the literature.

The present invention also provides a compound of the present invention (e.g., a compound of formula (I) or (II)) that is radiolabeled. When a compound of the present invention includes a ferrocene chelating group and the compound is labeled, it is appreciated that those of skill in the art understand that the ferrocene moiety can be converted to the corresponding labeled tricarbonyl complex, as disclosed in Cesati, R., J. Labeled Cpd. Radiopharm., 1999, 42, suppl. 1, s150–152 and references cited therein; to provide the radiolabeled compound. More specifically, the ferrocene moiety as shown below:

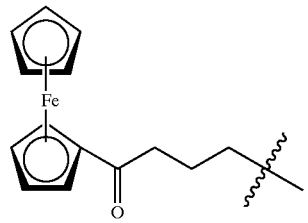

can be converted to the corresponding labeled tricarbonyl complex as shown below:

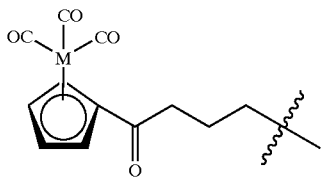

wherein
- M is a suitable radionuclide (e.g., Technetium-99m or Rhenium-186);

to provide the labeled compound.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound may be combined with one or more excipients and used in the form of ingestible tablets, buccal tablets, troches, capsules, elixirs, suspensions, syrups, wafers, and the like. Such compositions and preparations should contain at least 0.1% of the compound. The percentage of the compositions and preparations may, of course, be varied and may conveniently be between about 2 to about 60% of the weight of a given unit dosage form. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compound may be incorporated into sustained-release preparations and devices.

The present compounds may also be administered intravenously or intraperitoneally by infusion or injection. Solutions of a compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising a labeled or unlabeled compound of the present invention adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the labeled or unlabeled compound of the present invention plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Accordingly, the invention includes a pharmaceutical composition comprising a labeled or unlabeled compound of the present invention as described hereinabove; or a pharmaceutically acceptable salt thereof; and a pharmaceutically acceptable diluent or carrier.

Compounds of the present invention can be labeled using any of a number of techniques which are well known in the art. For example, a radioisotope can be incorporated into said compound or appended to said compound of the present invention using techniques well known in the art, for example, techniques analogous to those described in Arthur Murry III, D. Lloyd Williams; *Organic Synthesis with Isotopes*, vol. I and II, Interscience Publishers Inc., N.Y. (1958) and Melvin Calvin et al. *Isotopic Carbon* John Wiley and Sons Inc., N.Y. (1949). Preferably, a compound of the present invention may be labeled by appending a radioisotope of a halogen to the aromatic ring comprising DEF or to the linker (i.e., L) or the detectable chelating group (i.e., Det) in a compound of formula (III).

Additionally, a compound of the present invention can be labeled with a metal chelating group optionally comprising a radionuclide, such as a metallic radioisotope. Such chelating groups are well known in the art and include MAMA, BAT, polycarboxylic acids such as for example tricarbonyl complexes, diethylenetriaminepentaacetic acid, ethylenediaminetetraacetic acid, and the like, or analogs or homologs thereof; chelating agents such as ferrocene complexes, HYNIC, and fac[Tc(OH)$_2$(CO)$_3$]+ complexes; as well as the chelating groups disclosed in S. Meegalla et al. *J. Am. Chem. Soc.* 117 11037–11038, 1995 and in S. Meegalla et al. *Bioconjugate Chem.* 7:421–429, 1996. The chelating group or the radionuclide therein may be attached directly to a compound of the present invention, or may be attached to a compound of present invention by means of a divalent or bifunctional organic linker group. Such bifunctional linker groups are well known in the art and are preferably less than 50 angstroms in length. Examples of suitable linker groups include a divalent (C$_1$–C$_{10}$)alkyl, (C$_2$–C$_{10}$)alkenyl, or (C$_2$–C$_{10}$)alkynyl chain optionally comprising one or more —O—, —S—, or N(Z) in the chain and is optionally substituted on carbon with one or more oxo (=O). Additional suitable linker groups include 2-aminoethyl, 2-mercaptoethyl, 2-aminopropyl, 2-mercaptopropyl, ∈-amino caproic acid, 1,4-diaminobutane, and the like. Preferably, the bifunctional linker group is attached to a compound of the present invention at the bridgehead nitrogen which is substituted by the group R in the compounds of the present invention. A compound of the present invention bearing a linker group may conveniently be prepared from a compound of the present invention wherein R is hydrogen by alkylation of the bridgehead nitrogen. Suitable conditions for the alkylation of secondary amines are well known in the art. The linker group may also be attached at any synthetically feasible position.

Any metallic radioisotope capable of being detected in a diagnostic procedure (e.g., Tc-99m) or useful as a therapeutic radionuclide (e.g., Re-186) can be employed as a radionuclide. For example, suitable radioisotopes include: Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Cobalt-64, Erbium-169, Europium-152, Gadolinium-153, Gold-195, Gold-199, Hafnium-175, Hafnium-175–181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium. Preferably, technetium-99m may be useful for SPECT imaging studies, and rhenium-188, rhenium-186, copper-64 and yitrium-90 may be useful for radiotherapy of breast tumors.

The invention will be further described by reference to the following detailed examples.

EXAMPLES

Example 1

The ability to bind to sigma-1 or sigma-2 can be measured using methods currently known to those of skill in the art or using those techniques described in U.S. application Ser. No. 60/013717, filed Mar. 30, 1996; in U.S. application Ser. No. 09/142935, filed Sep. 17, 1998; or in U.S. application Ser. No. 09/528398, filed Mar. 20, 2000.

TABLE I

In vitro binding to σ$_1$ and σ$_2$ receptors

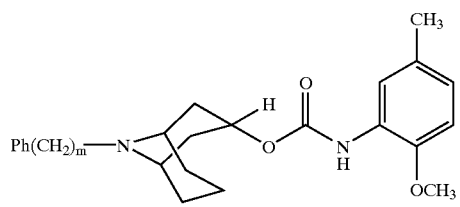

| Cmpd. | m | σ$_1$[a] | σ$_2$[b] |
|---|---|---|---|
| — | 1 | 92.5 ± 11 | 3.06 ± 0.83 |
| 6a | 2 | 59.9 ± 4.6 | 1.20 ± 0.10 |
| 6b | 3 | 72.9 ± 1.6 | 1.97 ± 0.12 |
| 6c | 4 | 65.5 ± 4.3 | 2.92 ± 0.21 |
| 6d | 5 | 17.3 ± 1.2 | 1.82 ± 0.19 |
| 6e | 6 | 213.6 ± 23.5 | 7.61 ± 0.41 |
| 6f | 7 | 229.9 ± 28.6 | 7.60 ± 0.18 |

[a]K$_i$ for inhibition of the binding of [$^3$H](+)-pentazocine to guinea pig brain homogenates (n = 3–5);
[b]K$_i$ for inhibition of the binding of [$^3$H]DTG to rat liver homogenates (n = 3).

Example 2

TABLE II

Binding of compounds of the present invention to σ₁ and σ₂ receptors.

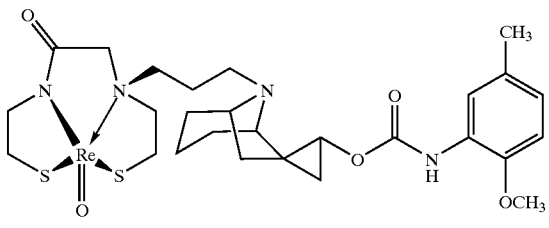

| Cmpd. | Q | $\sigma_1{}^a$ | $\sigma_2{}^b$ |
|---|---|---|---|
| 7a | I | 174.83 ± 6.71 | 140.69 ± 8.36 |
| 7b | N(H)C(=O)O-t-Bu | >1,000 | >1,000 |
| 7c | NH₂ | >1,000 | 7.78 ± 0.61 |

Example 3

TABLE III

Structure and in vitro binding data for a compound including a Re-oxo-MAMA chelating group:

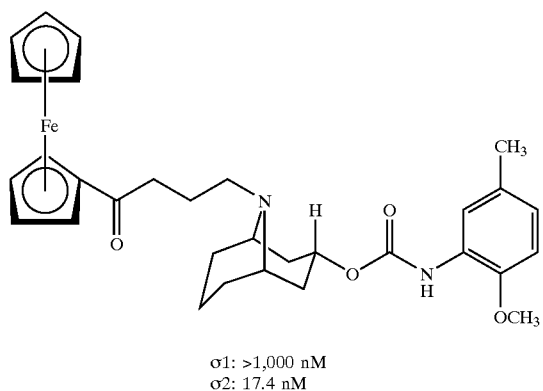

sigma-1 = >1,000 nM
sigma-2 = 14.4 nM

Example 4

TABLE IV

Structure and in vitro binding data for a compound including a ferrocene chelating group.

σ1: >1,000 nM
σ2: 17.4 nM

Example 5

TABLE V

Structure and in vitro binding data for compounds including a para-amino phenyl group.

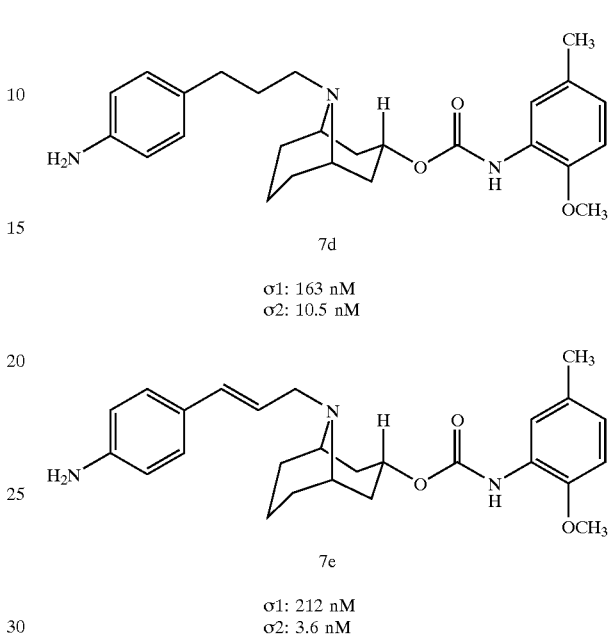

7d

σ1: 163 nM
σ2: 10.5 nM

7e

σ1: 212 nM
σ2: 3.6 nM

EXPERIMENTAL SECTION

Example 6

Preparation of compounds 6a–6f.

To a solution of N-(9-Benzyl-9-azabicyclo[3.3.1]nonan-3α-yl-N'-(2-methoxy-5-methylphenyl)carbamate (3 g) in methanol (200 mL) was added Pearlman's catalyst (0.3 g) and the suspension was hydrogenated on a Parr hydrogenation apparatus (50 psi hydrogen) for 20 hr. The catalyst was filtered and the solvent removed in vacuo to give a colorless oil that crystallized from ethylacetate/pentane, 1:1 to afford N-(9-azabicyclo[3.3.1]nonan-3α-yl)-N'-(2-methoxy-5-methylphenyl)carbamate as a white solid (50% yield); NMR (CDCl3/TMS) δ 7.93 (br s, 1H), 7.26 (s, 1H), 7.15 (br s, 1H), 6.77 (m, 2H), 5.00 (m, 1H), 3.84 (s, 3H), 3.42 (m, 2H), 2.32–2.34 (m, 2H), 2.30 (s, 3H), 1.28–2.05 (m, 8H). Alkylation with the corresponding phenylalkyl chloride gave compounds 6a–6f in 40–60% yield. All compounds were converted to the corresponding hydrochloride salt and recrystallized from ethanol.

6a. mp: 183.3–183.5° C.; NMR (CDCl3/TMS/free base); δ 7.96 (s, 1H), 7.19–7.31 (m, 6H), 6.72–6.79 (m, 2H), 5.09–5.16 (m, 1H), 3.82 (s, 3H), 2.45–3.10 (m, 8H), 2.29 (s, 3H), 0.90–1.90 (m, 8H).

6b. mp: 173–174° C.; NMR (CDCl₃/TMS/free base): δ 7.95 (s, 1H), 7.14–7.30 (m, 6H), 6.64–6.79 (m, 2H), 5.11–5.18 (m, 1H), 3.84 (s, 3H), 2.42–3.03 (m, 10H), 2.29 (s, 3H), 0.90–1.90 (m, 8H).

Re-MAMA-6b. ¹H-NMR (500 MHz; CDCl₃): 1.20–1.40 (m, 2H), 1.50–1.70 (m, 4H), 1.80–1.90 (m, 4H), 2.30 (s, 3H), 2.45 (p J=7 Hz, 2H), 2.50–2.70 (m, 2H), 2.90 (dd J=4, 13 Hz, 1H), 3.10 (br s, 2H), 3.10–3.30 (m, 3H), 3.45 (dt, J=3, 13 Hz, 1H), 3.60–3.70 (m, 1H), 3.85 (s, 3H), 3.90–4.00 (m, 1H), 4.1–4.20 (m, 2H), 4.50–4.60 (m, 1H), 4.60–4.70 (m, 1H), 5.10 (p, J=7 Hz, 1H), 6.70–6.80 (m, 2H), 7.10 (s, 1H), 7.90 (br s, 1H). C26H39N4O5S2Re: formula weight: 737.93; mass spectra: m/z: MF$^+$=737.46, M$^+$+2H=739.43; crystal data for Re-3: triclinic, Pi-$C_i^1$, a=7.166(2)Å, b=11.812(3)Å, and c=17.241(4)Å, α=103.297(9)°, β=91.82 (2)°, γ=93.33(3)°, V=1416.4(6)Å, Z=2, $D_x$=1.730 g/cm$^{-3}$, T=228(2)K. θrange 2.37 to 25.38°; reflections collected/unique: 5919/4721. The structural parameters were refined to convergence {$R_1$ (unweighted, based on F)=0.0802 and $\omega R_2$ (weighted, based on F2)=0.0906 for all reflections}.

6c. mp: 178–179° C.; NMR (CDCl$_3$/TMS/free base): δ 7.95 (s, 1H), 7.12–7.29 (m, 6H), 6.72–6.76 (m, 2H), 5.08–5.15 (m, 1H), 3.84 (s, 3H), 2.62 (m, 2H), 2.30–2.56 (m, 6H), 2.30 (s, 3H), 1.18–1.90 (m, 12H).

6d. mp: 191–1 92° C.; NMR (CDCl3/TMS/free base): δ 7.95 (s, 1H), 7.25–7.30 (m, 6H), 6.72–6.79 (m, 2H), 5.10–5.15 (m, 1H), 3.84 (s, 3H), 3.03 (m, 2H), 2.53–2.64 (m, 6H), 2.28 (s, 3H), 1.17–2.28 (m, 14H).

6e. mp: 180–180.5° C.; NMR (CDCl$_3$/TMS/free base): δ 7.95 (s, 1H), 7.25–7.30 (m, 6H), 6.72–6.79 (m, 2H), 5.10–5.15 (m, 1H), 3.84 (s, 3H), 3.03 (m, 2H), 2.53–2.64 (m, 6H), 2.28 (s, 3H), 1.17–2.28 (m, 16H).

6f. mp: 142–143.5° C.; NMR (CDCl3/TMS/free base): δ 7.95 (s, 1H), 7.25–7.30 (m, 6H), 6.72–6.79 (m, 2H), 5.10–5.15 (m, 1H), 3.84 (s, 3H), 3.03 (m, 2H), 2.53–2.64 (m, 6H), 2.28 (s, 3H), 1.17–2.28 (m, 18H).

Example 7

Preparation of the Ferrocene Complex and Compounds 7a–7e.

Ferrocene complex. To a solution of N-(9-azabicyclo[3.3.1] nonan-3a-yl)-N'-(2-methoxy-5-methylphenyl) carbamate (350 mg, 1.15 mmol) in toluene (10 mL) was added 4-bromobutyrylferrocene (385 mg, 1.15 mmol), potassium iodide (166 mg, 1.00 mmol), and triethylamine (500 mg, 4.94 mmol). The reaction mixture was refluxed overnight. Upon completion of reaction (as shown by TLC), the mixture was cooled to room temperature. Silica gel (1 g) was added, and the solvent was evaporated. The resulting solid was layered onto a silica gel column and eluted with 5% methanol in methylene chloride. The desired compound was isolated in 15 % yield (100 mg): mp 94–95° C.; $^1$H NMR (300 MHz, CDCl$_3$) δ 7.89 (s, 1H), 7.13 (s, 1H), 6.75–6.84 (m, 2H), 5.19–5.21 (m, 1H), 4.80 (s, 2H), 4.56 (s, 2H), 4.21 (s, 5H), 3.92 (s, 3H), 3.65 (s, 2H), 3.16–3.24 (m, 2H), 2.90–2.98 (m, 4H), 2.40–2.52 (m, 3H), 2.31 (s, 3H), 2.00–2.06 (m, 3H), 1.70–1.78 (m, 4H).

7a. NMR (CDCl$_3$/TMS/free base): δ 7.91 (br s, 1H), 7.68 (d, J=6 Hz, 2H), 7.29–7.30 (m, 3H), 6.79–6.87 (m, 2H), 5.17–5.24 (m, 1H), 3.88 (s, 3H), 3.71 (m, 2H), 3.27–3.40 (m, 4H), 2.59–2.62 (m, 4H), 2.33 (s, 3H), 1.28–2.12 (m, 8H).

7b. NMR (CDCl$_3$/TMS/free base): δ 7.98 (br s, 1H), 7.16 (s, 1H), 7.03 (d, J=5 Hz, 2H), 6.78–6.82 (m, 2H), 6.52–6.69 (m, 2H), 6.41 (s, 1H), 5.16 (quin, J=4 Hz, 1H), 3.87 (s, 3H), 3.09 (m, 2H), 2.45–2.81 (m, 6H), 2.33 (s, 3H), 1.63–2.04 (m, 4H), 1.58 (s, 9H), 1.21–1.55 (m, 4H).

7c. NMR (CDCl3/TMS/free base): δ 7.98 (br s, 1H), 7.16 (s, 1H), 7.03 (d, J=5 Hz, 2H), 6.78–6.82 (m, 2H), 6.52–6.69 (m, 2H), 5.16 (quin, J=4 Hz, 1H), 3.87 (s, 3H), 3.52 (br s, 2H), 3.09 (m, 2H), 2.45–2.81 (m, 6H), 2.33 (s, 3H), 1.27–1.94 (m, 8H).

Example 8

Preparation of Compounds 7d and 7e.

A solution of 4'-Butyloxycarbonylamino-3-phenylpropen-1-ol mesylate (1.62 g, 5 mmol), N-(9-azabicyclo[3.3.1]nonan-3α-yl)-N'-(2-methoxy-5-methylphenyl) carbamate (1.52 g, 5 mmol), and potassium carbonate (0.86 g, 6.25 mmol) in acetonitrile (10 mL) was stirred at reflux for 10 hrs. The mixture was concentrated in vacuo and the residue was suspended in water (25 mL) and extracted the product was extracted with dichloromethane (3×20 mL) and dried over Na$_2$SO$_4$. The Na$_2$SO$_4$ was removed by filtration. The product was purified by a silica gel column with CHCl$_3$/ethanol (9.75:0.25) to give the Boc-protected intermediate (1.31 g, 49%). NMR (CDCl$_3$/TMS): δ 7.95 (s, 1H), 7.14 (m, 2H), 7.11 (m, 3H), 6.79 (m, 2H), 6.42 (br s, 1H), 5.12, (quint, J=7 Hz, 1H), 4.17 (quart, J=6.4 Hz, 2H), 3.84 (s, 3H), 2.99–3.06 (m, 2H), 2.55–2.62 (m, 4H), 2.29 (s, 3H), 1.80–1.90 (m, 2H), 1.61–1.74 (m, 2H), 1.51 (s, 9H), 1.18–1.45 (m, 4H).

Deprotection was obtained by stirring a solution of the Boc-analog in trifluoroacetic acid (2 mL) and acetonitrile (4 mL) at room temperature for 1 hr to give the 4-amino analog (7d) in quantitative yield: NMR (CDCl$_3$/TMS): δ 7.95 (s, 1H), 7.13 (s, 1H), 6.98 (m, 2H), 6.79 (m, 2H), 6.76 (m, 2H), 5.12, (quint, J=7 Hz, 1H), 4.17 (quart, J=6.4 Hz, 2H), 3.54 (br s, 2H), 3.84 (s, 3H), 2.99–3.06 (m, 2H), 2.55–2.62 (m, 4H), 2.29 (s, 3H), 1.80–1.90 (m, 2H), 1.61–1.74 (m, 2H), 1.51 (s, 9H), 1.18–1.45 (m, 4H). Hydrogenation over palladium/charcoal in ethanol (20 mL) gave 7e in quantitative yield.

Example 9

The following illustrate representative pharmaceutical dosage forms, containing a compound of the present invention ('Compound X'), for therapeutic, prophylactic, and/or diagnostic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |

| | |
|---|---|
| Polyethylene glycol 400 | 200.0 |
| 01 N Sodium hydroxide solution (pH adjustment to 7.0–7.5) | q.s. |
| Water for injection | q.s. ad 1 mL |
| (vi) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |
| (vii) Tablet 1 | mg/tablet |
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (viii) Tablet 2 | mg/tablet |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |
| (ix) Capsule | mg/capsule |
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |
| (x) Injection 1 | mg/mL |
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |
| (xi) Injection 2 | mg/mL |
| 'Compound X' | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |
| (xii) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art. Although specific quantities of "Compound X" are shown in the above illustrative examples, it is to be understood that the compounds can be present in any ratio provided the final formulation possesses the desired biological properties.

It is believed that compounds of the present invention can provide detectably labeled ligands that can selectively bind to carrier cells and can be quantified by using functional imaging techniques such as positron emission tomography (PET), single photon emission computed tomography (SPECT), and functional magnetic resonance imaging (fMRI). Said components have the potential to noninvasively assess the proliferative status of known or suspected tumor cells or cells subject to hyperplasia, in bladder, colon, prostate, breast, lung, gut, pancreas, reproductive system, brain and the like. Additional labeled compounds of the present invention that comprise a therapeutic radionuclide (e.g., Re-186) can also be used to treat cancer or abnormally dividing cells, by selectively inhibiting their proliferation.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

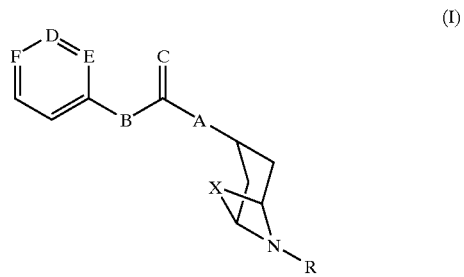

wherein

R is aryl-Y—;

Y is $(C_2-C_{14})$alkenyl, aryl is optionally substituted with one or more halo, OH, $(C_1-C_6)$alkyl, $(C_1-C_6)$alkoxy, $(C_1-C_6)C(O)$, $(C_1-C_6)$alkyl-S, $NH_2$, SH, $N(Z)_2$;

A is NH, O or S;

B is NH, O, or S;

C is O or S;

D is CH;

E is CH;

F is CH; and

X is $(CH_2)_2$, $(CH_2)_3$ or CH=CH;

each Z is H or $(C_1-C_6)$alkyl;

wherein the ring comprising F=D–E is optionally substituted with one or more halo, OH, $(C_1-C_6)$alkyl, $(C_1-C_6)$alkoxy, $(C_1-C_6)C(O)$, $(C_1-C_6)$alkyl-S, $NH_2$, SH, $N(Z)_2$; wherein Z is H or $(C_1-C_6)$alkyl, or methylene dioxy (—$OCH_2O$—);

or a pharmaceutically acceptable salt thereof.

2. The compound of claim 1 that is detectably-labeled.

3. The compound of claim 2 wherein the label comprises a radiocuclide.

4. The compound of claim 1 wherein B is NH and A is O.

5. The compound of claim 1 wherein the ring comprising F=D—E is substituted with $(C_1-C_6)$alkyl, $(C_1-C_6)$alkoxy, or any combination thereof.

6. The compound of claim 1 wherein the ring comprising F=D—E is substituted with methyl, methoxy, or any combination thereof.

7. The compound of claim 1 wherein aryl is phenyl.

8. The compound of claim 1 wherein aryl is para-amino phenyl.

9. The compound of claim 1 wherein Y is n-ethenylene, n-propenylene, n-butenylene, n-pentenylene, n-hexenylene, or n-heptenylene.

10. The compound of claim 1 wherein X is $(CH_2)_3$.

11. A compound of formula (I):

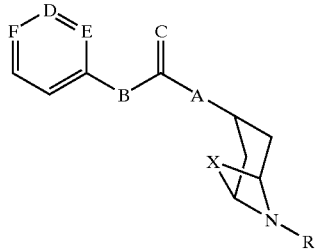

(I)

wherein

R is a —L-Det;

L is a divalent $(C_2-C_{10})$alkyl, $(C_2-C_{10})$alkenyl, or $(C_2-C_{10})$alkynyl chain optionally comprising one or more —O—, —S—, or N(Z) in the chain and optionally substituted on carbon with one or more oxo (=O);

A is NH, O or S;

B is NH, O, or S;

C is O or S;

D is CH;

E is CH;

F is CH;

X is $(CH_2)_2$, $(CH_2)_3$ or CH=CH;

wherein the ring comprising F=D—E is optionally substituted with one or more halo, OH, $(C_1-C_6)$alkyl, $(C_1-C_6)$alkoxy, $(C_1-C_6)$C(O), $(C_1-C_6)$alkyl-S, $NH_2$, SH, $N(Z)_2$;

each Z is H or $(C_1-C_6)$alkyl;

Det is

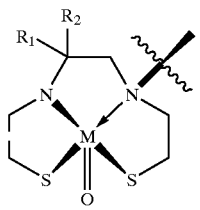

wherein

M is Technetium-99m or Rhenium-186;

$R_1$ and $R_2$ are each independently H or together are oxo;

or a pharmaceutically acceptable salt thereof.

12. The compound of claim 11 wherein B is NH and A is O.

13. The compound of claim 11 wherein the ring comprising F=D—E is substituted with $(C_1-C_6)$alkyl, $(C_1-C_6)$alkoxy, or any combination thereof.

14. The compound of claim 11 wherein the ring comprising F=D—E is substituted with methyl, methoxy, or any combination thereof.

15. The compound of claim 11 wherein X is $(CH_2)_3$.

16. The compound of claim 11 which is a compound of formula (III):

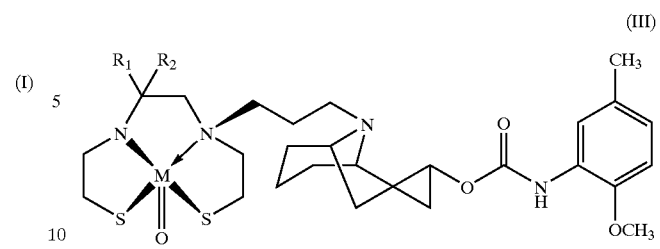

(III)

wherein

M is Technetium-99m or Rhenium-186; and $R_1$ and $R_2$ are each independently H or together are oxo.

17. A compound of formula (I):

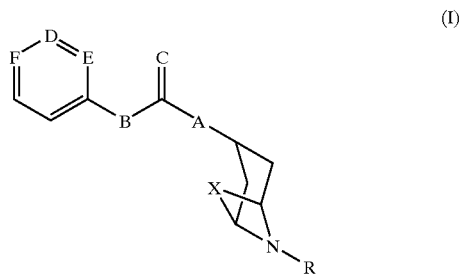

(I)

wherein

R is a —L-Det;

L is a divalent $(C_2-C_{10})$alkyl, $(C_2-C_{10})$alkenyl, or $(C_2-C_{10})$alkynyl chain optionally comprising one or more —O—, —S—, or N(Z) in the chain and optionally substituted on carbon with one or more oxo (=O);

A is NH, O or S;

B is NH, O, or S;

C is O or S;

D is CH;

E is CH;

F is CH;

X is $(CH_2)_2$, $(CH_2)_3$ or CH=CH;

wherein the ring comprising F=D–E is optionally substituted with one or more halo, OH, $(C_1-C_6)$alkyl, $(C_1-C_6)$alkoxy, $(C_1-C_6)$C(O), $(C_1-C_6)$alkyl-S, $NH_2$, SH, $N(Z)_2$;

Det is

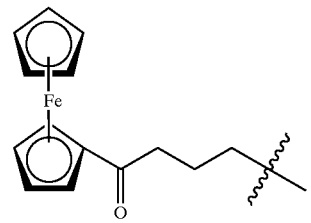

and each Z is H or $(C_1-C_6)$alkyl.

18. A compound of the formula:

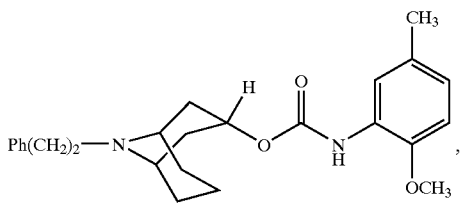

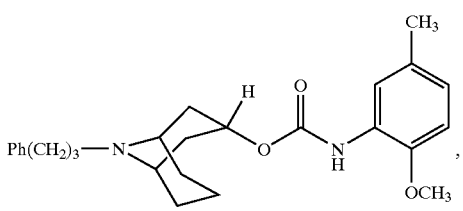

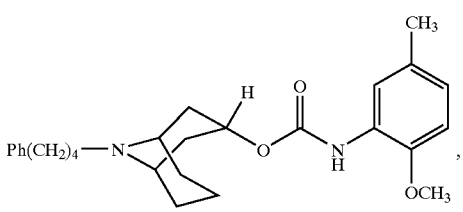

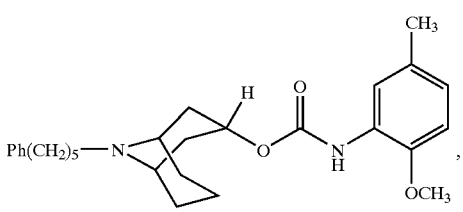

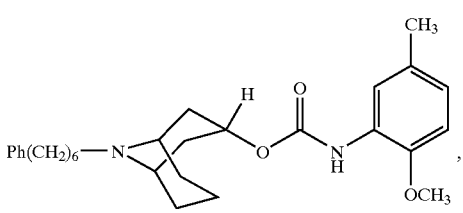

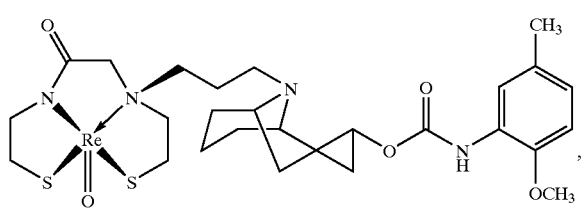

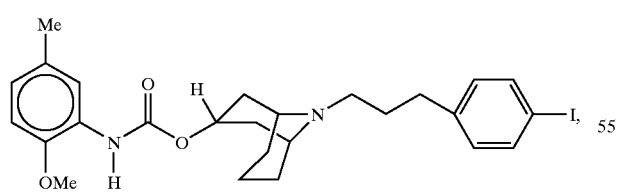

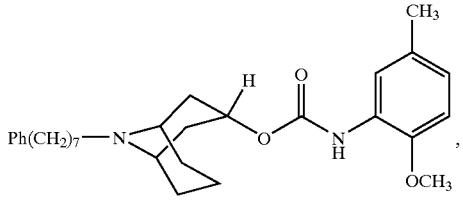

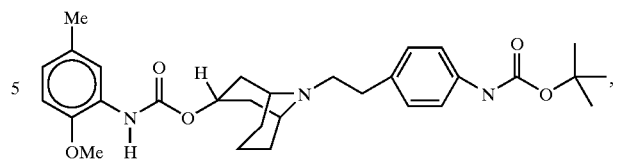

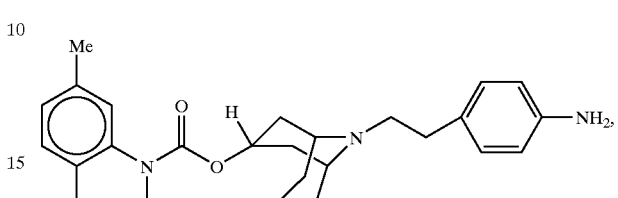

or

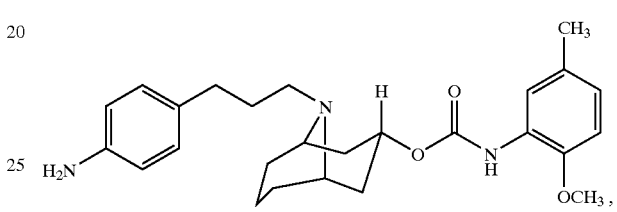

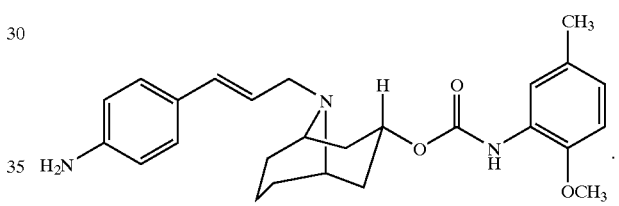

19. A pharmaceutical composition comprising a compound of any one of claims 1, 11, 17, and 18; and a pharmaceutically acceptable carrier.

20. A method to determine the proliferative status of a cancer cell comprising:

(a) administering to a human afflicted with a solid tumor, an amount of a detectably-labeled compound of any one of claims 1, 11, 17, and 18; and (b) determining the extent to which the compound binds to cells of the tumor, the extent providing a measure of the proliferative status of the cells.

21. A method to image a solid tumor comprising:

(a) administering to a human afflicted with a solid tumor, an amount of a detectably-labeled compound of any one of claims 1, 11, 17, and 18; and (b) detecting the presence of the detectably-labeled compound.

* * * * *

UNITED STATES PATENT AND TRADEMARK OFFICE
CERTIFICATE OF CORRECTION

PATENT NO. : 6,669,925 B1
DATED : December 30, 2003
INVENTOR(S) : Mach et al.

It is certified that error appears in the above-identified patent and that said Letters Patent is hereby corrected as shown below:

Column 2,
Lines 45-54, Formula I should appear as:

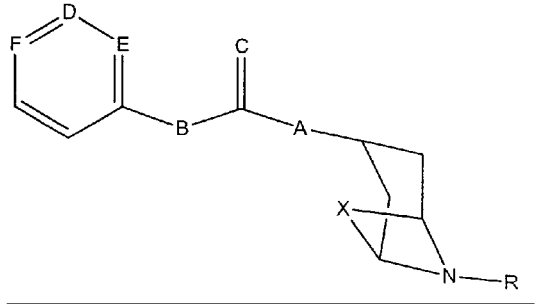

Column 18,
Line 54, should read -- a radionuclide. --

Signed and Sealed this

Thirteenth Day of July, 2004

JON W. DUDAS
*Acting Director of the United States Patent and Trademark Office*